(12) United States Patent
Sexton et al.

(10) Patent No.: US 6,626,171 B2
(45) Date of Patent: Sep. 30, 2003

(54) POWDER/LIQUID METERING VALVE

(75) Inventors: Frederick Sexton, Fair Haven, NJ (US); Perry A. Genova, Chapel Hill, NC (US); Akwete L. Adjei, Bridgewater, NJ (US)

(73) Assignee: IEP Pharmaceutical Devices Inc., Raleigh, NC (US)

( * ) Notice: Subject to any disclaimer, the term of this patent is extended or adjusted under 35 U.S.C. 154(b) by 300 days.

(21) Appl. No.: 09/854,127

(22) Filed: May 11, 2001

(65) Prior Publication Data

US 2001/0039948 A1 Nov. 15, 2001

Related U.S. Application Data
(60) Provisional application No. 60/204,070, filed on May 12, 2000.

(51) Int. Cl.[7] ............................................... A61M 11/00
(52) U.S. Cl. ........................ 128/200.23; 128/200.14; 128/200.19; 128/203.12; 222/635
(58) Field of Search .................. 128/200.14, 200.19, 128/200.23, 200.22, 203.12; 222/402.2, 635; 239/338, 380

(56) References Cited

U.S. PATENT DOCUMENTS

| | | | |
|---|---|---|---|
| 1,858,735 A | | 5/1932 | Goodsell |
| 3,416,709 A | | 12/1968 | Schultz et al. |
| 3,731,851 A | | 5/1973 | Rauh |
| 3,733,010 A | * | 5/1973 | Riccio ........................ 222/635 |
| 3,844,322 A | | 10/1974 | Stoutenberg |
| 3,989,165 A | * | 11/1976 | Shaw et al. .................... 222/23 |
| 4,053,087 A | | 10/1977 | Lack et al. |
| 4,205,822 A | | 6/1980 | Bernat |
| 4,526,215 A | | 7/1985 | Harrison et al. |
| 4,621,718 A | | 11/1986 | DeCarolis |
| 4,777,852 A | | 10/1988 | Herman et al. |
| 4,984,923 A | | 1/1991 | Ota |
| 5,033,463 A | | 7/1991 | Cocozza |
| 5,082,148 A | | 1/1992 | Dunning |
| 5,201,308 A | | 4/1993 | Newhouse |
| 5,277,175 A | | 1/1994 | Riggs et al. |
| 5,295,479 A | | 3/1994 | Lankinen |
| 5,301,664 A | | 4/1994 | Sievers et al. |
| 5,309,955 A | | 5/1994 | Torterotot |
| 5,347,999 A | | 9/1994 | Poss et al. |
| 5,421,492 A | | 6/1995 | Barger et al. |
| 5,477,849 A | | 12/1995 | Fry |
| 5,490,615 A | | 2/1996 | Robbins et al. |
| 5,507,420 A | * | 4/1996 | O'Neill ........................ 222/635 |
| 5,520,073 A | | 5/1996 | Bakula et al. |
| 5,526,962 A | | 6/1996 | Huggenberger |
| 5,546,932 A | | 8/1996 | Galli |
| 5,568,884 A | | 10/1996 | Bruna |
| 5,575,192 A | | 11/1996 | Eggert |
| 5,593,069 A | * | 1/1997 | Jinks ........................... 222/246 |
| 5,617,845 A | | 4/1997 | Poss et al. |
| 5,641,096 A | | 6/1997 | Robbins et al. |

(List continued on next page.)

FOREIGN PATENT DOCUMENTS

| | | |
|---|---|---|
| EP | 0 826 386 A3 | 8/1992 |
| EP | 0 826 386 A2 | 8/1992 |
| WO | WO 98/51359 | 11/1998 |

*Primary Examiner*—Weilun Lo
*Assistant Examiner*—Michael Mendoza
(74) *Attorney, Agent, or Firm*—Frommer Lawrence & Haug, LLP; Ronald R. Santucci

(57) ABSTRACT

The metering valve which includes a material reservoir formed generally above a load bearing bottom hollow, with a toroidal gas chamber formed thereabout. Both the gas chamber and the material reservoir include metering spindles which allow the material to be dispensed and gas to be mixed precisely in a mixing chamber, and dispensed through an orifice.

17 Claims, 4 Drawing Sheets

U.S. PATENT DOCUMENTS

Figure 1A:
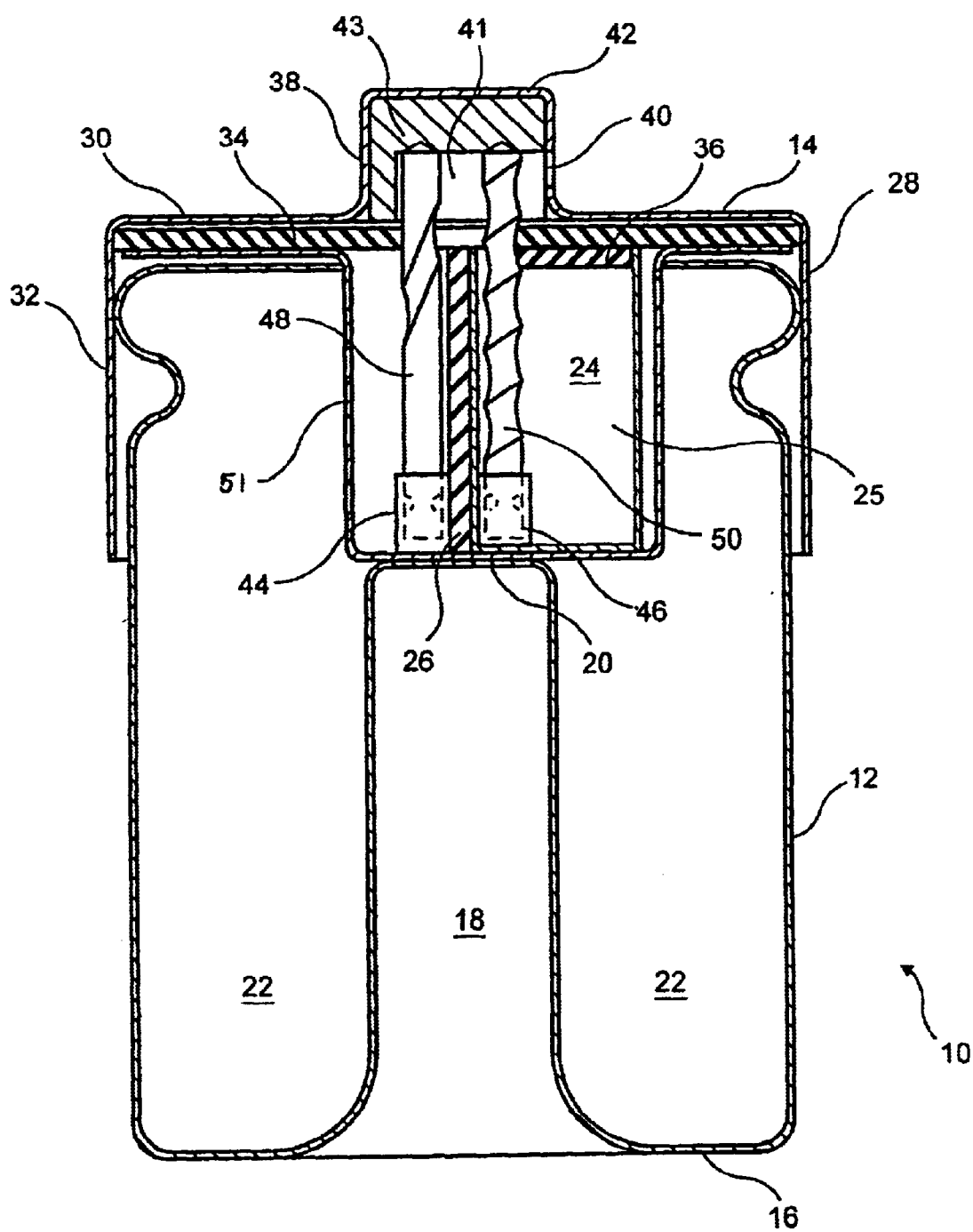

| | | |
|---|---|---|
| RE35,552 E | 7/1997 | Lankinen |
| 5,655,523 A | 8/1997 | Hodson et al. |
| 5,673,685 A | 10/1997 | Heide et al. |
| 5,765,552 A | 6/1998 | Zanen et al. |
| 5,570,616 A | 8/1998 | Thompson et al. |
| 5,839,622 A | 11/1998 | Bicknell et al. |
| 5,924,417 A * | 7/1999 | Braithwaite ............ 128/203.15 |
| 5,934,510 A | 8/1999 | Anderson |
| 6,032,836 A * | 3/2000 | Hiscocks et al. ........ 222/402.2 |
| 6,240,918 B1 * | 6/2001 | Ambrosio et al. ..... 128/203.15 |

* cited by examiner

POWDER/LIQUID METERING VALVE

This invention claims priority from Provisional application No. 60/204,070 titled "Powder/Liquid Metering Valve" filed on May 12, 2000, the disclosure of which incorporated herein by reference.

BACKGROUND OF THE INVENTION

1. Field of the Invention

This invention relates to a metering valve and more particularly, to a metering valve utilizing a metered amount of a fluid or compressed gas carrier combined in a mixing chamber with a metered amount of a medicament and the like. The ingredients are measured and transported by a dosing means under conditions whereby a gaseous medicament dispersion is formed.

2. Description of the Prior Art

Metered dose inhalers (MDIs first introduced in 1956) are self-contained packages usually consisting of an aluminum can and a lid with a metering valve crimped on it. The formulation inside the can usually consists of propellant(s) and drugs, either in solution or suspension, along with excipients to aid in stability and dosimetry of the product. The valve system is fitted to an actuator along with a mouthpiece, which links the canister to the patients' mouth. When the valve is actuated a pre-metered volume of the formulation is released through the valve into the mouthpiece. The latent heat of vaporization of the volatile propellant provides the energy for atomization of droplets of product released from the valve. Usually, a partial evaporation of about 10–20% of propellant vehicle occurs immediately after expulsion of product from the nozzle. It is this violent evaporation of propellant that causes instant breakup of aerosol droplets into fine respirable particles, usually $\leqq 10\ \mu m$ subsequently yielding particles with a mass median aerodynamic diameter (MMAD) in the range between 3 and 8 $\mu m$.

Chloroflurocarbons (CFCs) are substituted halogenated alkanes used extensively in the pharmaceutical industry because they are inert, non-toxic and possess enough vapor pressure to warrant their use as drug delivery carriers in pharmaceutical aerosols. Aerosolized beta-agonists and anti-allergic compounds were the first series of pharmaceuticals to use CFCs as propellants for drug delivery to the lung. For these products, appropriate combinations of CFC propellant blends are necessary to insure a proper balance between vapor pressure and device performance. Such propellant combinations enable the formation of a fine spray upon actuation of the delivery mechanism. The use of a metering valve allows delivery of a predetermined volume of the product upon actuation. Hence, these delivery systems are also referred to as metered-dose inhalers (MDIs). These CFC propellants are suggested to interfere with stratospheric ozone protection. In 1991, the total consumption of CFCs in medical aerosols was estimated to be about 0.5% of the total worldwide consumption of these materials, but despite such low levels of CFCs consumed in MDIs, environmentally conscious groups are committed to see a total ban on the production and use of these products. There are medical, ethical and social consequences for abandoning CFCs totally before suitable alternatives are available.

The need to replace CFCs in clinical and industrial applications based on scientific, medical and environmental mandates, including the Montreal Protocol, has led to large research programs to identify and test acceptable substitutes. A number of possible alternative propellants have been rejected for safety reasons. Some, for example compressed gases, simply do not have the physical properties needed to achieve uniform doses from MDIs. Others, for example hydrocarbons, are unsuitable because of their flammability. Yet others are toxic because they cause drowsiness or affect the heart. Attention is now being focussed on two hydrofluoroalkanes (HFAs), HFA-134a and HFA-227, respectively called tetrafluorethane and heptafluoropropane. These propellants appear to have the necessary physical properties, do not cause ozone depletion, are non-flammable and, most importantly, appear to be non-toxic when compared to CFCs at equivalent doses. Establishing the suitability of these alternative propellants before introducing them for use in MDIs involves a lengthy and highly regulated process. The significant progress made thus far is a reflection of the substantial development effort made by the pharmaceutical industry to phase out CFCs from MDIs while maintaining the range of treatment options available for patients.

Although HFAs possess several desirable properties which make them suitable, effective and safe alternatives to CFC propellants, they nonetheless are greenhouse gases and have the potential to cause undue global warming (e.g., warming of oceans, and water evaporation, which would further delay the transmission of heat). Thus, future drug delivery systems should concentrate on technology platforms that are truly inert to the environment.

More recently, electronically-controlled devices which use aqueous formulations in a manner similar to conventional MDIs have been developed. Piezo devices produce a spray out of a single drop of drug solution. The drug is metered by a nozzle onto a mesh or grid. The device usually consists of an actuator head, a housing, a piezo-electric element, and a mesh. The liquid droplet on the mesh is energized by the piezo-electric element using an alternating voltage thus causing vibrations of drug molecules in the droplet. The vibrations are amplified by the housing. This causes the mesh and the liquid droplet to also vibrate subsequently resulting in spray formation. Particle size thus depends on the flow rate of drug solution onto the mesh. Particle size distribution of the aerosolized particles depend also on the hole size in mesh, number of holes in the mesh, and magnitude of the vibrational energy.

Nebulized inhalation systems are aqueous formations which are aerosolized with the aid of external energy. The process converts water droplets to the vapor phase, which is inhaled by the patient. Unlike MDIs, the composition of these systems resembles injectable formulations and is administered with specific devices, namely compressors and atomizers. The formulations generally contain dissolved drug but suspensions of the drug together with other inactive excipients may be neubulized for stability and taste reasons. At the time of use, the solution is poured into the nebulizer, which generally contains an ultrasonic probe or an air jet source to aid aerosolization. A mouthpiece or hood traps the resulting particles so that tidal breathing may be used by the patient to inhale the drug. Nebulizers are not compact like MDIs and they are often too bulky for ambulatory use. In addition, they take several minutes to hours to complete the dosing. In spite of this limitation, nebulizers offer several significant advantages. They contain mainly water as a vehicle and therefore present no great safety concerns in regard to formulation toxicity.

Nebulizers present a variety of dosing schemes and dose volumes so that they are flexibly adaptable for drugs whose activity is so low as to require several milligram to gram quantities to obtain measurable pharmacologic effects. However, there are a number of technical and clinical limitations concerning nebulized drug technologies. Sterility of drug formulations, the need for ancillary hardware, example generator, and their suitability to non-ambulatory care because of size, places them at a disadvantage.

Unlike MDIs and nebulizers, where drug solution or suspension is initially released as a "wet" spray, DPIs constitute formulations and devices where a predetermined dose of active, either alone or in a blend with some carrier like lactose, is released as a fine mist of dry powder for inhalation. These systems differ significantly from MDIs and nebulizers in that they do not contain any liquid media (e.g., propellant or water). The drug is formulated in a manner so that it readily disperses into particles of respirable size range (i.e. $\leq 10$ $\mu$m). The powder dispersion is initiated either by inspiration or by some external source, e.g., an electronic vibrator included with the device hardware. In older DPI technologies, the formulation to be inhaled was packaged in single dose units, for example in hard gelatin capsules. The unit dose capsules were manually placed into the device. After breakage of the shell immediately prior to use, the dose was inhaled through a grid placed in the path of the powder. Newer DPI devices are reservoir systems capable of providing multiple dosing without a manual transfer of dosing units into the device.

Prior art includes U.S. Pat. No. 5,839,622 to Bicknell et al.; U.S. Pat. No. 5,641,096 to Robbins et al.; U.S. Pat. No. 5,568,884 to Bruna; U.S. Pat. No. 5,490,615 to Robbins et al.; U.S. Pat. No. 5,437,999 to Poss et al.; U.S. Pat. No. 5,082,148 to Dunning; U.S. Pat. No. 3,731,851 to Rauh; and U.S. Pat. No. 3,416,709 to Shultz et al.

OBJECTS AND SUMMARY OF THE INVENTION

It is therefore an object of the present invention to provide a powder/liquid metering valve which reliably and consistently delivers the desired dose of dry or liquid medicament to a user in a reasonably short period of time.

It is therefore a further object of the invention to provide a powder/liquid metering valve which is reproducibly filled with medicament during the life of the product.

It is therefore a still further object of the present invention to provide a powder/liquid metering valve that uses a propellant that is inert, non-flammable and non-toxic.

It is therefore a still further object of the present invention to provide a powder/liquid metering valve that uses a propellant which does not raise significant environmental concerns.

It is therefore a still further object of the present invention to provide a powder/liquid metering valve combined with a metered dose inhaler to be portable in size.

It is therefore a still further object of the present invention to provide a powder/liquid metering valve for a metered dose inhaler which has an operation substantially identical to that of current CFC/HFA based systems.

These and other objects are attained by providing a powder/liquid metering valve which includes two functioning metering elements that work in a synchronized manner with each other to dispense precise quantities of a gas phase and a medicament or other material from separate chambers/reservoirs. The first element being a gas metering spindle with an appropriately designed helix profile that when rotated partially or fully along its long axis when positioned against a sealing element it serves to throttle an appropriate liquefied or compressed gas through a mixing chamber and eventually out through an orifice in the mixing chamber positioned perpendicular to the entry point of spindle. Coincident with the movement of the gas metering spindle or shortly thereafter a second spindle element, a drug or material metering spindle, is designed with an appropriate helix profile such that when it is in contact with a reservoir of active ingredient, in the form of a dry powder, solution or suspension, the rotational movement of the drug metering spindle carries forward a precise metered quantity of material contained in the reservoir and presents the material to the mixing chamber simultaneously or with a delay versus the presentation of the expanding gas. The rotation of the drug metering spindle in association with its sealing element will ensure only the precise desired quantity of material is metered out. The helical profile of the drug metering spindle is designed such that with pressure applied by the user and the subsequent rotation of the spindle, the drug metering spindle can throttle material into and out of the mixing chamber before during and after the material is presented to the mixing chamber. The sequencing of the presentation of materials from the gas metering and drug metering spindles serves to create a negative pressure at the interface of the spindles at the start of the metering process followed by a full mixing of the material in the gas stream including deagglomeration and particle/droplet size formation and finally a cleansing of the drug metering spindle prior to its return to its at rest position.

The orientation of the entry of material from the gas metering and drug metering spindle into the mixing chamber is parallel to the long axis of each spindle. The drug reservoir may include a collapsible bellow or other means suitable for the purpose of maintaining a constant pressure on the medicament provided to the metering element. The exit orifice port may be perpendicular or parallel to the long axis of the spindles.

BRIEF DESCRIPTION OF THE DRAWINGS

Further objects and advantages of the invention will become apparent from the following description and claims, and from the accompanying drawings, wherein:

FIGS. 1A and 1B are cross-sectional views of the powder/liquid metering valve of the present invention in a metered dose inhaler.

FIG. 2 is a plan view of the helical metering spindle of the present invention including both rotational drives.

FIG. 3 is a plan view of the helical metering spindle of the present invention including one rotational drive.

FIG. 4 is a plan view of the helical metering spindle of the present invention beside one rotational drive.

FIG. 5 is an upper perspective view of one of the rotational drives of the present invention.

FIG. 6 is a graph depicting gas/drug medicament release times and overlap of release times during inhaler use.

DETAILED DESCRIPTION OF THE PREFERRED EMBODIMENT

Referring now to the drawings in detail wherein like numerals refer to like elements throughout the several views, one sees that FIGS. 1A and 1B are side cross-sectional views of the present invention. For purposes of this disclosure, the metering valve assembly 10 is being illustrated as a metered dose inhaler and will be referred to as such. However, the metering valve has other applications as will be apparent to those skilled in the art. The metering valve assembly 10 is generally defined by cylindrical container wall 12 which is bounded by upper wall 14 and lower wall 16. Lower wall 16 includes a centrally located load bearing bottom hollow 18 which is upwardly bounded by load bearing bottom contour 20. Toroidal gas chamber 22, which typically includes pressurized carbon dioxide, nitrogen, or air is formed about load bearing bottom hollow 18.

Drug or material reservoir 24 may contain liquid or powdered medicament, or even medicament in the form of a lotion. Drug reservoir 24 is formed generally between load bearing bottom contour 20 and upper wall 14, and is bounded by spindle seal 26 which passes through a rotational axis of metered dose inhaler 10. Drug reservoir (24) includes a collapsible bellow (25) or other means suitable for purpose to maintain a constant pressure on the medicament in the drug reservoir 24 so as to allow for reproducibly filling the drug or metering spindle 50, whose operation will be further discussed.

Ferrule 28 is partially cylindrical with upper planar wall 30 which forms upper wall 16 and further includes cylindrical wall 32 which extends over a portion of cylindrical container wall 12 to form a seal therewith. Main seal 34 is formed immediately underneath upper planar wall 30. Drug reservoir seal 36 is formed immediately beneath main seal 34 at the top of drug reservoir 24. Cylindrical walls 38 rise from upper planar wall 30 with orifice 40 formed thereon. Orifice 40 can also be formed on the top of cylindrical walls 38, so as to provide a communication path parallel to the rotational axis of metered dose inhaler 10. In FIG. 1B, orifice 40 can also be formed so as to provide a communication path perpendicular to the rotational axis of the metered dose inhaler 10. Orifice 40 provides a medicament communication path from drug mixing chamber 41 of metering valve 42 to the user.

Metering valve 42 mainly consists of, a mixing chamber, spindle bearing, and two metering spindles. Spindle bearing assembly 43 is formed at a top of cylindrical walls 38 with two bearings which are aligned with gas spindle bearing assembly 44 and drug spindle bearing assembly 46 on opposing sides of spindle seal 26. Gas metering spindle 48 is journaled for rotation within gas spindle bearing assembly 44 and spindle bearing assembly 43. Likewise, drug metering spindle 50 is journaled for rotation in drug spindle bearing assembly 46 and spindle bearing assembly 43. Spindle stabilizing assembly 51 is formed about drug reservoir 24 and gas metering spindle 48 in order to structurally stabilize gas metering spindle 48 and drug metering spindle 50. The user pushing down on spindle bearing assembly 43 causes the metering spindles 48, 50 to rotate.

Figure 2:
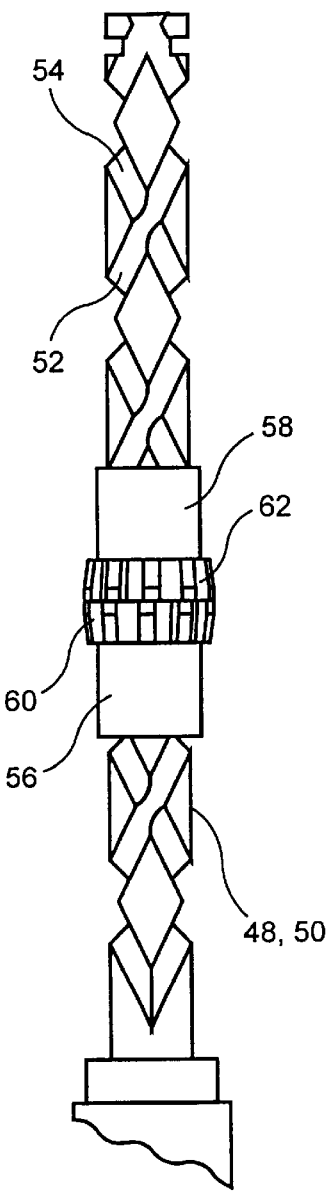
Figure 3:
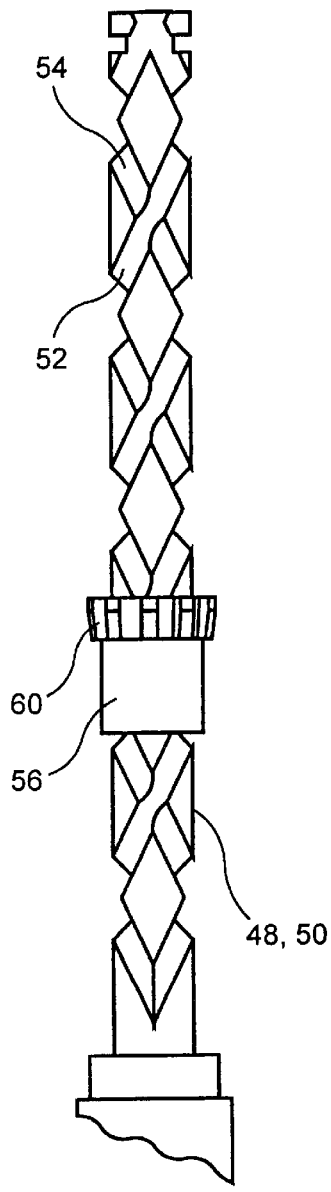
Figure 4:
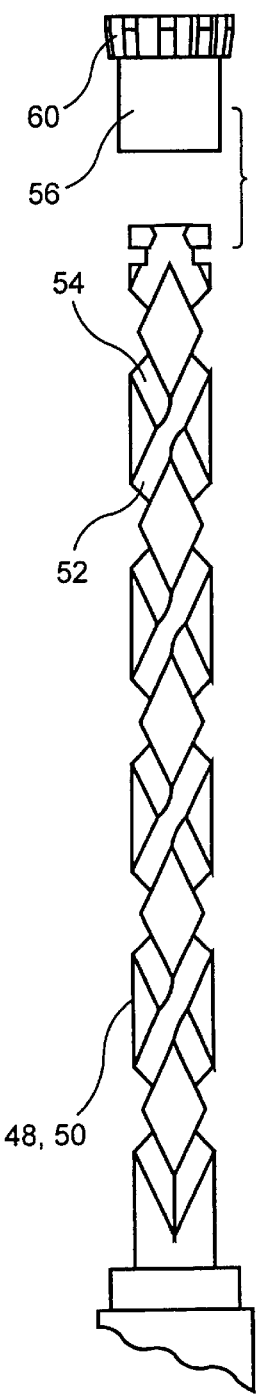
Figure 5:
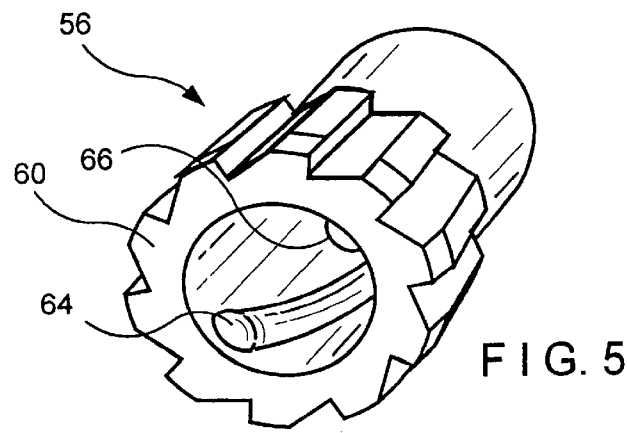
Figure 6:
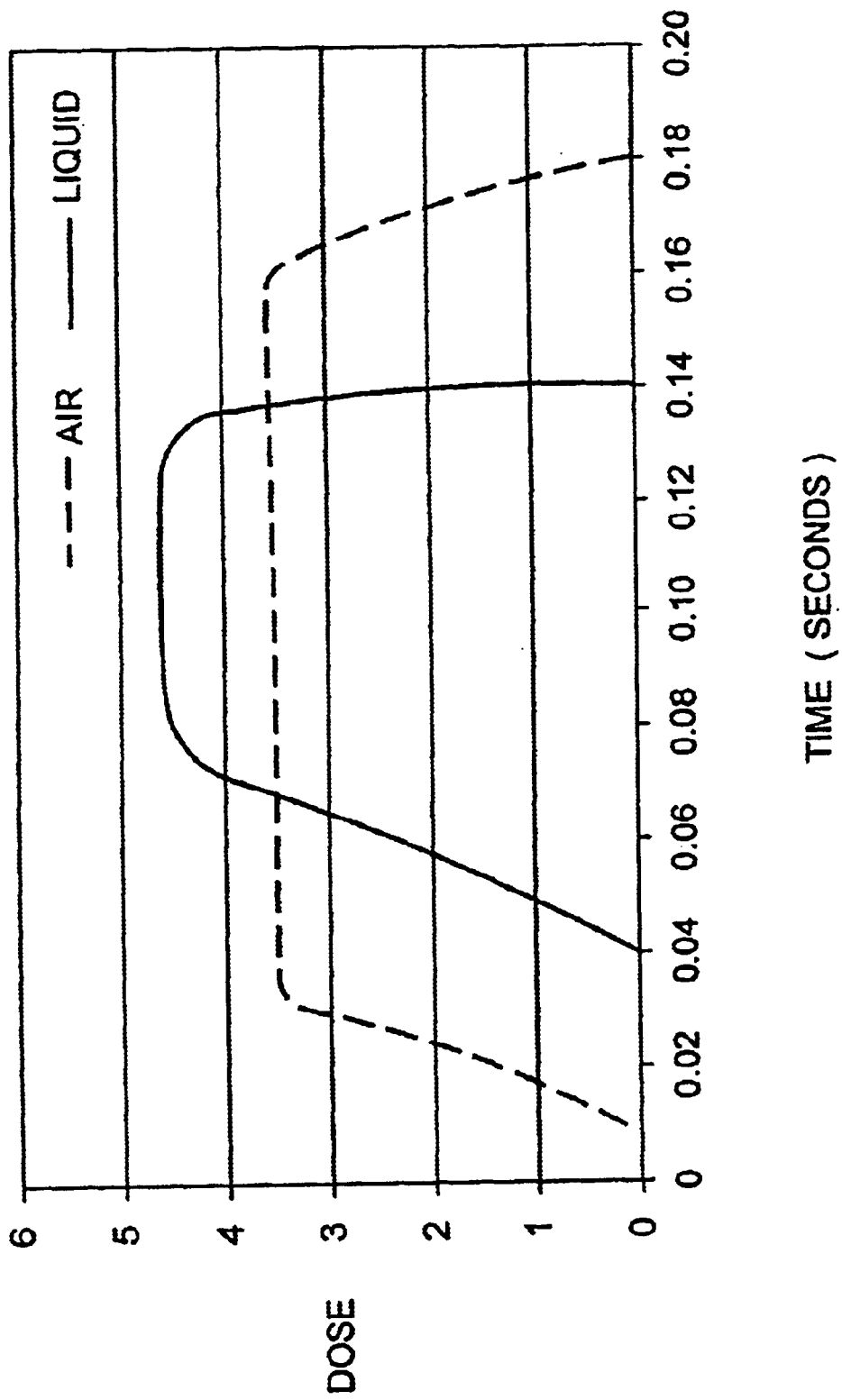

As shown in FIGS. 2, 3 and 4, metering spindles 48, 50 include opposing double helical grooves 52, 54. Counter-rotating rotational drive elements 56, 58 are generally cylindrical with a central aperture through which metering spindles 48, 50 pass, and further include circumferential grooved sections 60, 62, respectively. Furthermore, rotational drive elements 56, 58, as shown in FIG. 5, include internally protruding ridges 64, 66 which are complementary to helical grooves 52, 54 in order to cause counter-rotation of drive elements 56, 58 and collinear movement along metering spindles 48, 50 in response to the rotation of metering spindles 48, 50. This collinear movement is limited by a stop member to regulate the resulting dose. In order to regulate or limit the resulting dose, a dead stop can be set around metering spindles 48, 50 to limit the co-linear movement of drive elements 56, 58 (similar to the construction of a typical butane lighter).

Figure 1B:
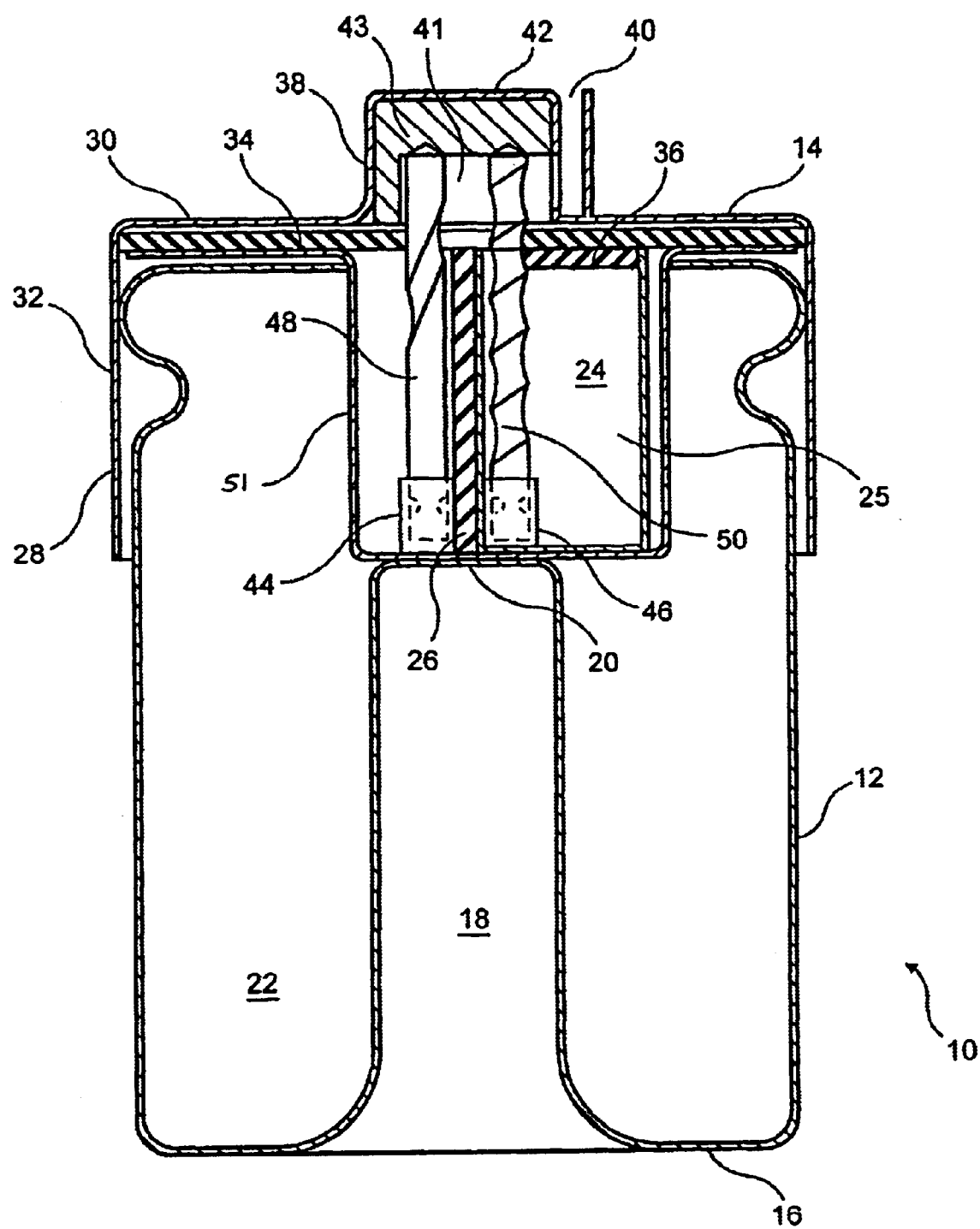

Upon rotation of spindles 48, 50 in FIGS. 1A and 1B, gas is released from gas chamber 22 followed on by medicament from drug chamber 24 in mixing chamber 41 of metering valve 42. Gas release would follow-on medicament release. Extended gas release over medicament release ensures adequate atomization, additional nozzle clearance, and cleansing of the drug metering spindle 50 prior to its return to its at-rest position. FIG. 6 is a graph depicting gas/drug medicament release times and overlap of release times during inhaler use. Specific timing of the overlap is not critical although duration of the medicament release may be directly proportional to the volume or dose size required. As shown it is envisioned that the release of the gas would precede that of the medicament and follow on afterwards. This ensures adequate atomization in addition to cleansing mixing chamber 41 and orifice 40.

Thus the several aforementioned objects and advantages are most effectively attained. Although a single preferred embodiment of the invention has been disclosed and described in detail herein, it should be understood that this invention is in no sense limited thereby, and its scope is to be determined by that of the appended claims.

What is claimed is:

1. A metering valve for metering the dispensing of a material, said metering valve comprising:

a gas reservoir containing a gas;

a material reservoir containing material to be dispersed;

a spindle bearing assembly;

a gas metering spindle which rotates in response to user pressure on said spindle bearing assembly thereby throttling gas from said gas reservoir;

a mixing chamber positioned with entry ports in order to receive gas and material for the mixing thereof and a pathway for dispensing the material to the user; and a material metering spindle which rotates in response to user pressure on said spindle bearing assembly conveys a predetermined amount of material from said material reservoir to said mixing chamber for mixing with said gas and dispersed therefrom.

2. The metering valve of claim 1 wherein said gas reservoir contains pressurized gas.

3. The metering valve of claim 2 wherein said pressurized gas is carbon dioxide, nitrogen, or air.

4. The metering valve of claim 1 wherein said material reservoir contains liquid medicament.

5. The metering valve of claim 1 wherein said material reservoir contains powdered medicament.

6. The metering valve of claim 1 wherein said material reservoir contains medicament in the form of a lotion.

7. The metering valve of claim 1, wherein said material reservoir reproducibly fills said mixing chamber.

8. The metering valve of claim 1, wherein said material reservoir further includes a means for applying pressure on said material so as to reproducibly fill said material metering spindle.

9. The metering valve of claim 8 wherein said means for pressurizing comprises a collapsible bellow.

10. The metering valve of claim 1 further including a gas spindle bearing assembly whereby said gas spindle bearing assembly provides a pathway for gas throttled by said gas metering spindle.

11. The metering valve of claim 1 wherein said material mixing chamber further includes an exit orifice port.

12. The metering valve of claim 11 wherein said exit orifice port is parallel to the rotational axis of said gas metering spindle.

13. The metering valve of claim 11 wherein said exit orifice port is perpendicular to the rotational axis of said gas metering spindle.

14. The metering valve of claim 1 further including a material spindle bearing assembly wherein said material spindle bearing assembly provides a pathway for material throttled by said material metering spindle.

15. The metering valve of claim 1 wherein said material metering spindle acts contemporaneously with said gas metering spindle.

16. The metering valve of claim 1 wherein said material metering spindle acts non-contemporaneously with said gas metering spindle.

17. A method of dispensing a material comprising the steps of providing with the metering valve of claim 1 whereby the sequencing of the presentation of materials from said material metering spindle and said gas metering spindle creates a negative pressure at the start of the metering process followed by a full mixing of the material in the gas stream including deagglomeration and particle droplet size formation and a dispensing therefrom.

* * * * *